United States Patent [19]

Ho et al.

[11] 4,006,240
[45] Feb. 1, 1977

[54] ALCOHOL AVERSION PROCESS BY ENZYME INHIBITION

[76] Inventors: Andrew K. S. Ho, c/o Dept. of Basic Sciences, Peoria School of Medicine University of Illinois, Peoria, Ill. 61606; Benjamin Kissin, c/o Kings County Addictive Disease Hospital, 600 Albany Ave., Brooklyn, N.Y. 11203

[22] Filed: Mar. 19, 1975

[21] Appl. No.: 560,018

[52] U.S. Cl. .................................. 424/263; 424/329
[51] Int. Cl.² ................. A61K 31/44; A61K 31/14
[58] Field of Search ............................ 424/263, 329

[56] References Cited
OTHER PUBLICATIONS

Hemsworth et al.—Chem. Abst. vol. 73 (1970) p. 86260b.

*Primary Examiner*—Sam Rosen
*Attorney, Agent, or Firm*—R. E. Carnahan; R. H. Uloth

[57] ABSTRACT

A biochemical explanation for preferential alcohol consumption is proposed involving excessive cholinergic activity in brain tissue. A process by which alcohol aversion can be induced involving treatment with a choline acetylase inhibitor is provided.

5 Claims, No Drawings

ALCOHOL AVERSION PROCESS BY ENZYME INHIBITION

FIELD OF THE INVENTION

The present invention involves a drug bio-affecting and body treating process employing an organic active ingredient of the pyridine or quinoline classes.

DESCRIPTION OF THE PRIOR ART

Drug treatment of alcoholism has taken three approaches. Tranquilizers have been widely used during alcohol withdrawal to relieve the symptoms involved which include delirium, hallucinations, and tremors. Alcohol withdrawal treatment is a heroic measure, however, involving hospitalization and prolonged rehabilitation periods. Treatment processes which deal with the disease before it reaches such an actute stage as to require hospitalization have long been sought. Among these are conditioned response or aversion therapy which involve administering an alcoholic beverage and at the same time a powerful nausea producing agent like emitine or apomorphine. Repeated treatments with such a combination are intended to develop a conditioned reflexed loathing for alcohol in any form. This method has not, however, met with widespread success. More widely known and used are so-called deterrent agents such as disulfiram and citrated carbimide. A patient regularly taking one of these compounds finds that ingestion of alcohol in any form quickly produces pounding headache, flushing, and usually violent nausea. This method, however, requires substantial motivation and cooperation on the part of the patient and has not proven to be dependable with chronic alcoholics.

The present invention is directed at treatment of what is believed to be the cause of the disease. We have found that in animals exhibiting a preference for alcohol consumption as their principal fluid intake that enzymatic imbalances in the brain involving the cholinergic system are extant which result in elevated acetylcholine concentrations in brain tissue. The latter is believed to lead to a compulsion for alcohol ingestion. The present invention involves the method of treatment which reduces the acetylcholine concentrations in the brain and thus relieves the compulsion for the consumption of alcohol which is believed to be one of the principal causes of the syndrome.

SUMMARY OF THE INVENTION

The present invention involves the systemic administration of a drug substance having specific inhibitory activity for the enzyme choline acetylase to a mammal having an inherent propensity for excessive alcohol consumption. The latter expression refers to mammals having a neurobiochemical lesion or abnormality which induces a compulsion to consume alcohol in above normal amounts when both alcohol and water are made available to the mammal. For example, the C57Bl/6J strain of mouse is a genetically pure strain which consumes alcohol in preference to water in a free choice situation (water, and 5% aqueous ethanol being equally accessible for drinking purposes) in amounts substantially higher than other strains of mice. For the C57Bl/6J strain, a large preponderance of any given population of these animals in a free choice situation will select a 5 or 10% ethanol solution for 75% or more of their total fluid intake. In employing these animals for experimental purposes, 80% or more of a given population will be found to exhibit such preference for 5 or 10% ethanol solution. The belief is widely accepted that a large segment of physiologically dependent human alcoholics possess a biochemical lesion or abnormality which mobilizes the compulsion for consuming alcohol in excessive amounts. The present process is applicable to such mammals and should be distinguished from alcohol conditioned aversion processes which are based upon psychological means such as conditioned avoidance through various forms of punishment.

By "systemic administration," is meant any form of drug administration or dosage which results in transport of the drug through the blood stream to the site of action within the body. Examples of methods of systemic administration are oral administration where the drug is absorbed from the gastrointestinal tract into the blood stream, the various forms of parenteral administration such as intravenous administration where the drug is injected directly into the blood stream, and intramuscular or intraperitoneal injection where the drug is injected into a body tissue and absorbed therefrom into the blood stream. Other modes of systemic administration include rectal administration, buccal administration, and sublingual administration.

The expression "specific physiologically acceptable inhibitor," with reference to the enzyme choline acetylase, is intended to refer to inhibitors of the enzyme activity thereof which are non-toxic and physiologically tolerable to the tissues with which they come in contact during systemic administration. Additionally the effect thereof is reversible; that is, the enzyme is not destroyed but rather rendered temporarily inoperable while the inhibitor is present. The term is intended to refer to substances which interfere with the activity of this particular enzyme but not of other enzymes, and to exclude general enzyme poisons or non-specific inhibitors such as the heavy metal ions, silver, cadmium, and mercury, organic mercurials, N-ethylmaleimide, and inhibitors of protein synthesis such as acetoxycyclohex- imide.

A number of specific physiologically acceptable inhibitors of the enzyme choline acetylase are known, but their application to the treatment of alcoholism has not been previously suggested. The following references are cited with respect to inhibitors of choline acetylase which may be employed according to the present invention.

Cavallito, Yun, Smith, and Foldes, J. Med. Chem., 12, 134–138 (1969).
Cavallito, Yun, Kaplan, Smith and Foldes, ibid, 13, 221–224 (1970).
Baker and Gibson, ibid, 14, 315–322 (1971).
D. Malthe-Sorenssen, et al., Biochemical Pharmacol., 23, 577–586 (1974).
E. F. Domino, et al., Neuropharmacology, 12, 549–561 (1973).

The foregoing are cited only for exemplary purposes and any non-toxic physiologically acceptable specific inhibitor of the enzyme choline acetylase which is effective to cause alcohol aversion may be employed in the present invention.

DETAILED DESCRIPTION OF THE INVENTION

More specifically, the present invention is concerned with the systemic administration to mammals having an inherent propensity for excessive alcohol consumption of a compound having the formula ArCH=CHHet or ArC≡CHet, a pharmaceutically acceptable acid addition or quaternary ammonium salt of one of these substances, acryloylcholine, or acetylsecohemicholinium-3. The latter two substances have the following formulas wherein X is an anion as defined below.

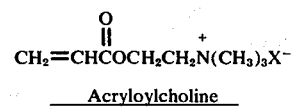

Acryloylcholine

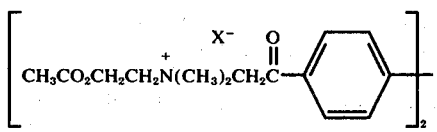

Acetylsecohemicholinium-3

The aforesaid acid addition salts have the formula ArCH=CHHet·HA, and ArC≡CHet·HA and the quaternary ammonium salts have the formula ArCH=CHHet·RX and ArC≡CHet·RX.

In the foregoing formulas, Ar is an aromatic substituent and preferably phenyl, 1-naphthyl, 2-naphthyl, indanyl, or indolyl each of which may be unsubstituted or substituted by up to 2 substituents selected from the group consisting of fluorine, chlorine, bromine, iodine, lower alkyl having 1 to 4 carbon atoms, and lower alkoxy having 1 to 4 carbon atoms. From 0 to 2 substituents may be present.

Het is a basic nitrogen containing heterocyclic group and preferably 2-pyridyl, 3-pyridyl, 4-pyridyl, 2-quinolyl, 3-quinolyl, 4-quinolyl or any of the foregoing pyridyl and quinolyl groups substituted on carbon by from 0 to 1 lower alkyl group having 1 to 4 carbon atoms.

HA is an acid which forms a stable acid addition salt with the basic heterocyclic moiety Het to provide a pharmaceutically acceptable acid addition salt of the substances of the formula ArCH=CHHet and ArC≡CHet. By "pharmaceutically acceptable" is meant a salt which is stable and absorbable by the mammalian organism under the conditions of formulation and use and in which the HA moiety does not contribute significantly to the toxicity or pharmacologic action of the resulting salt in the quantity in which it is present in the dosage of the salt which is employed. Examples of acids which form pharmaceutically acceptable salts are hydrochloric, hydrobromic, sulfuric, phosphoric, nitric, methanesulfonic, p-toluenesulfonic, acetic, benzoic, citric, tartaric, propionic, lauric, muccic, etc.

The pharmaceutically acceptable quaternary ammonium salts of the present invention contain an R moiety attached to the basic nitrogen atom of Het thereby forming a cation and an X anion. The anion is pharmaceutically acceptable as defined above and may be, by way of example, chloride, bromide, sulfate, phosphate, nitrate, mesylate, tosylate, acetate, benzoate, citrate, propionate, laurate, mucate, iodide, etc. They are prepared by reaction of the ArCH=CHHet or ArC≡CHet base with a reactive ester of the formula RX or XRX wherein R is an unsubstituted or a monosubstituted alkyl or alkylene group having from 1 to 18 carbon atoms and preferably lower alkyl having from 1 to 4 carbon atoms, aralkyl having from 7 to 12 carbon atoms such as benzyl, methylbenzyl, naphthylmethyl and naphthylethyl or hydroxy substituted groups having from 1 to 8 carbon atoms and preferably 1 to 4 carbon atoms wherein the substituent, when present, is hydroxy, and carboxamido. Examples of suitable reactive esters are methyl iodide, ethyl bromide, methanesulfonic acid, toluenesulfonic acid, dimethylsulfate, triethylphosphate, hexamethylene dibromide, 2-bromoethanol, etc.

Criteria applicable to the selection of choline acetylase inhibitors for use in the present invention involve first, choosing a compound which is highly potent in vitro employing a rabbit or rat brain choline acetylase preparation for assay. The methods referred to in the foregoing references which are modifications of that of McCaman and Hunt, Journal of Neurochemistry, 12, 253 (1965) may be employed using either the rat brain or rabbit brain preparations. The inhibitors are tested in the in vitro preparation at various concentrations and a graph is prepared of percent inhibition versus the logarithm of the inhibitor concentration and that concentration which reduces the enzyme activity by 50% ($I_{50}$) is determined by interpolation from the graph. It is preferred to employ inhibitors having an $I_{50}$ value of less than $10^{-4}M$.

Other criteria for operative compounds according to the present invention deal with matters of physiological absorption and transport within the mammalian organism which can best be determined by routine experiment. Effective compounds to cause alcohol aversion are those having the foregoing level of in vitro activity and which are absorbed on oral or parenteral administration as described above and are distributed by the circulating blood to the active site within the organism. It is believed that the active site is in the brain and that the compound must be transported by the blood to the nerve tissue of the brain across the so-called blood brain barrier in order to be effective. An animal assay involving rats trained on a conditioned avoidance procedure suitable to estimate transport to the brain has been described by Goldberg and Ciofalo, Psychopharmacologia (Berlin) 14, 142–149 (1969).

According to the Goldberg and Ciofalo method, amphetamine administered intraperitoneally in a dose of 2.0 mg./kg. to a group of rats trained on a conditioned avoidance procedure causes about a 75% increase in the response rate for a 3 hr. session. Substances which decrease cholinergic function, either by blocking the effect of acetylcholine or by preventing synthesis thereof, as is the case with choline acetylase inhibitors, augment the stimulating effect of amphetamine on the conditioned avoidance response when administered concomitantly therewith. Cholinergic stimulants on the other hand significantly antagonize the response to amphetamines. Since amphetamine is believed to exert its stimulating effect on motor activity directly on the brain, it is believed that any substance such as the choline acetylase inhibitors useful in the present invention which modify the action of amphetamine are also reaching the brain and exerting their effect therein. Thus, amphetamine potentiation in a conditioned avoidance procedure in rats may be used to select compounds having the quality of being transported by the blood across the blood brain barrier to the nervous tissue of the brain.

The compounds identified in Tables I, II, and III are specific inhibitors of choline acetylase in vitro and according to the foregoing criteria may be employed in the present invention. In all instances where ethylenic compounds are employed, the trans-isomer is preferred. For compounds of the actylene series, of course, geometric isomers do not exist.

TABLE I

NAPHTHYLVINYLPYRIDINE CHOLINE ACETYLASE INHIBITORS

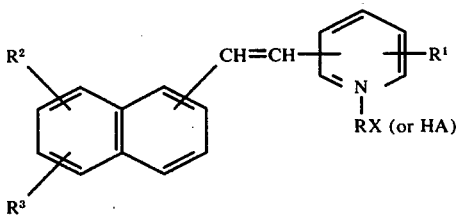

| Naphthyl Position | Pyridyl Position | RX (or HA) | R¹ | R² | R³ |
|---|---|---|---|---|---|
| 1 | 4 | HCl | H | H | H |
| 1 | 4 | CH₃I | H | H | H |
| 2 | 4 | CH₃I | H | H | H |
| 1 | 4 | CH₃I | H | 2-OH | H |
| 1 | 2 | CH₃I | H | H | H |
| 2 | 4 | base* | H | H | H |

*Where "base" is used in Tables I, II, and III, reference is made to the free base of the formula given absent the RX (or HA) substituents.

TABLE II

STILBAZOLE CHOLINE ACETYLASE INHIBITORS

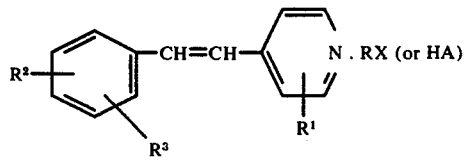

| RX (or HA) | R¹ | R² | R³ |
|---|---|---|---|
| CH₃I | H | H | H |
| n-C₆H₁₃Br | H | H | H |
| C₆H₅CH₂Cl | H | H | H |
| CH₃I | 3-CH₃ | H | H |
| Br(CH₂)₆Br* | H | H | H |
| CH₃I | H | 4-CH₃ | H |
| CH₃I | H | 4-F | H |
| CH₃I | H | 4-Cl | H |
| CH₃I | H | 4-Br | H |
| CH₃I | H | 3-Cl | H |
| CH₃I | H | 2-Cl | H |
| CH₃I | H | 3-Br | H |
| CH₃I | H | 3-Cl | 4-Cl |
| CH₃I | 3-CH₃ | H | H |
| CH₃I | 3-CH₃ | 3-Cl | H |
| CH₃I | 3-CH₃ | 2-Cl | H |
| CH₃I | 3-CH₃ | 3-Cl | 4-Cl |
| CH₃I | 3-C₂H₅ | H | H |
| base | H | 4-CH₃ | H |
| HCl | H | 3-Cl | H |
| p-CH₃C₆H₄SO₃H | H | 3-CH₃ | H |
| base | H | 3-CH₃O | H |
| p-CH₃C₆H₄SO₃H | H | 3-Cl | 4-Cl |

*Hexamethylene-1,6-bis-N,N'-(4-styrylpyridinium)dibromide

TABLE III

MISCELLANEOUS CHOLINE ACETYLASE INHIBITORS

| Ar | ArCH = CHHet . RX(or HA) Het | RX (or HA) |
|---|---|---|
| 5-indanyl | 4-pyridyl | CH₃I |
| phenyl | 2-quinolyl | CH₃I |

TABLE III-continued

MISCELLANEOUS CHOLINE ACETYLASE INHIBITORS

| Ar | ArCH = CHHet . RX(or HA) Het | RX (or HA) |
|---|---|---|
| phenyl | 4-quinolyl | CH₃I |
| 1-naphthyl* | 4-pyridyl | CH₃I |
| 1-naphthyl | 3-methyl-4-pyridyl | CH₃I |
| 1-naphthyl | 4-pyridyl | HOCH₂CH₂Br |
| 1-naphthyl | 4-pyridyl | ICH₂CONH₂ |
| 3-chlorophenyl | 3-methyl-4-pyridyl | HOCH₂CH₂Br |
| 3-bromophenyl | 3-methyl-4-pyridyl | HOCHCH₂Br |
| 3-indolyl | 4-pyridyl | CH₃I |
| phenyl | 4-quinolyl | CH₃I |
| phenyl | 4-quinolyl | HOCH₂CH₂Br |
| 1-naphthyl | 4-quinolyl | HOCH₂CH₂Br |

*1-Methyl-4-(1-naphthylethynyl)pyridinium iodide; applicable formula is ArC CHet . RX The dose of the choline acetylase inhibitor when administered according to the present invention is selected to cause effective aversion to alcohol consumption. Effective aversion is intended to mean either the complete lack of compulsion to consume alcohol or at least a reduction of the compulsion to a point where the subject may consume alcohol in a strictly elective manner without being dependent thereon. The dose is also selected to be substantially free of undesirable side effects. By this is meant that the side effects are at most of a trivial nature and unimportant relative to the benefit derived from the treatment. One effect of excessive dosage with a choline acetylase inhibitor is a reduction in water consumption. One manner of estimating a suitable dose therefore is to administer various doses to a normal mammal, or to one having an excessive inherent propensity to consume alcohol if it is possible to entirely eliminate alcohol consumption for a period of several days, measure the water intake during the dosage period, and to select that dose for treatment which has no significant effect on normal water intake. The maximum dose which is without effect on normal water intake is generally a sufficient dose to reduce alcohol consumption in a mammal having an excessive propensity for consumption of alcohol.

DESCRIPTION OF SPECIFIC EMBODIMENTS

EXAMPLE 1

Ethanol Aversion in C57B1/6J Mice

The dose of trans-4-[2-(1-naphthyl)vinyl]pyridine hydrochloride which has no significant effect on water or total fluid intake of these animals was determined to be 2 mg./kg. This was determined by intraperitoneal injection of trans-4-[2-(1-naphthyl)vinyl]pyridine hydrochloride at 12 hourly intervals during the test period at various dosage concentrations for various groups of mice. A graph was then prepared in which the mg./kg. of water consumed was plotted against the dose administered. From this graph, it was possible to determine that dose which has no significant effect on water intake. This is the dose that was employed to ascertain the effect on alcohol intake in a free choice situation.

Adult male C57B1/6J mice weighing 20–25 g. were then placed into individual cages equipped with two small drinking tubes, one filled with water and the other with 5% ethanol in water. Food, water and alcohol solution were available ad libitum and the daily consumption of each was recorded at 10 a.m. The positions of the tubes were interchanged daily and different tubes were ocassionally substituted. After a period of 4 days to establish a reference base for alcohol and water consumption respectively, the animals were treated by intraperitoneal injection with 2 mg./kg. of body weight of trans-4-[2-(1-naphthyl)vinyl]-pyridine hydrochloride at 12 hourly intervals on the 5th and 6th days. Drug treatment was terminated on the 6th day and the animals were kept for an additional two days. The average values of water, 5% alcohol, and total fluid intake for each of these 8 days of the experiment are shown in the following table.

TABLE IV

| DAY | | DAILY FLUID CONSUMPTION OF C57B1/6J MICE | | | | | | | |
|---|---|---|---|---|---|---|---|---|---|
| | | BASELINE | | | | NVP ADMINISTERED | | | |
| | | 1 | 2 | 3 | 4 | 5 | 6 | 7 | 8 |
| 5% ALCOHOL | ML/KG | 118±4 | 116±4 | 133±5 | 135±5 | 60±2* | 82±3* | 112±3 | 117±3 |
| ALCOHOL | % | 63% | 62% | 67% | 65% | 34% | 43% | 60% | 64% |
| WATER | ML/KG | 70±3 | 71±3 | 65±2 | 72±3 | 117±4 | 111±4 | 76±3 | 65±3 |
| TOTAL | ML/KG | 188 | 187 | 199 | 207 | 177 | 193 | 187 | 183 |

N = 8 *P<0.001

It is evident from the data contained in Table IV that the total daily fluid intake remained substantially constant during the experimental period. In the absence of drug treatment, 5% ethanol constituted about 65% of the total daily fluid intake. On the days of drug treatment, namely, the 5th and 6th days, alcohol consumption decreased to about 42% of the daily fluid intake. On cessation of drug treatment, the water and alcohol intakes returned substantially to their pretreatment values.

In order to ascertain whether the effect of NVP treatment on alcohol consumption indicated the existence of an elevated concentration of acetylcholine in the brain of the C57B1/6J mouse, an experiment was conducted in which the acetylcholine concentrations in the brain of this strain of mouse and that in a strain of mouse which exhibits no preference for alcohol, namely the DBA/2J strain were determined. The brains were removed from a group of C57B1/6J mice and from a group containing a corresponding number of DBA/2J mice and the acetylcholine levels were determined by a bioassay method using the isolated guinea pig ileum preparation (Bentley and Shaw, J. Pharmacology and Experimental Therapeutics, 106, 193 (1952)). The acetylcholine was extracted into 10% trichloroacetic acid as described by Hebb (Handbuch der Pharmakologie, 15, Chapter 3, G. B. Koelle, sub-ED., 1963). It was found that the acetylcholine concentrations in the brain of the C57B1/6J mice were substantially higher than in the DBA/2J mice. Mean values of 3.30 ± 0.20 microgram/gram of tissue and 2.20 ± 0.2 micrograms/gram of tissue were obtained respectively. Thus the C57B1/6J mice were found to have approximately 45% higher concentration of acetylcholine in their brains than the DBA/2J mice.

What is claimed is:
1. The method for inducing alcohol aversion in a mammal having an inherent propensity for excessive alcohol consumption which comprises systemic administration to said mammal of a non-toxic dose effective to cause alcohol aversion of a specific physiologically acceptable inhibitor of the enzyme choline acetylase wherein said inhibitor is a compound selected from the group consisting of

ArCH=CCHet,

ArC≡CHet, the pharmaceutically acceptable acid addition and quaternary ammonium salts of each, acryloylcholine, and acetylsecohemicholinium-3, wherein
Ar is phenyl, napthyl, indanyl, indolyl, each of which may be substituted by from 0 to 2 substitutents selected from the group consisting of fluorine, chlorine, bromine, iodine, lower alkyl having 1 to 4 carbon atoms, and lower alkoxy having 1 to 4 carbon atoms,
Het is 2-pyridyl, 3-pyridyl, or 4-pyridyl, each of which may be carbon substituted by from 0 to 1 lower alkyl groups having 1 to 4 carbon atoms.
2. The method of claim 1 wherein said dose is less than that which alters the water intake of said mammal in the absence of alcohol consumption.
3. The method of claim 1 wherein said inhibitor is trans-4-[2-(1-naphthyl)vinyl]pyridine or a pharmaceutically acceptable acid additon or quaternary ammonium salt thereof.
4. The method of claim 3 wherein said inhibitor is trans-1-methyl-4-[2-(1-naphthyl)vinyl]pyridinium iodide.
5. The method of claim 3 wherein said inhibitor is trans-4-[2-(1-naphthyl)vinyl]pyridine hydrochloride.

* * * * *